United States Patent [19]

Bruno

[11] Patent Number: 5,174,087
[45] Date of Patent: Dec. 29, 1992

[54] SUTURE ANCHOR ASSEMBLY PACKAGING SYSTEM

[75] Inventor: Joseph A. Bruno, Canton, Mass.

[73] Assignee: Mitek Surgical Products, Inc., Norwood, Mass.

[21] Appl. No.: 838,357

[22] Filed: Feb. 19, 1992

[51] Int. Cl.⁵ .................. A61B 17/00; A61L 17/02
[52] U.S. Cl. .................. 53/430; 206/63.3; 606/228
[58] Field of Search .......... 53/430, 116; 206/63.3, 206/63.5; 606/228

[56] References Cited

U.S. PATENT DOCUMENTS

| 3,759,376 | 9/1973 | Lisowski | 53/430 X |
| 4,034,850 | 7/1977 | Mandel et al. | 206/63.3 |
| 4,572,363 | 2/1986 | Alpern | 206/63.3 |
| 4,699,271 | 10/1987 | Lincoln et al. | 206/63.3 |
| 5,078,730 | 1/1992 | Li et al. | 606/228 |

Primary Examiner—James F. Coan
Attorney, Agent, or Firm—Pandiscio & Pandiscio

[57] ABSTRACT

A packaging system for a pre-assembled suture anchor assembly of the sort comprising of a suture anchor, a length of suture threadingly engaging the suture anchor and a pair of surgical needles attached to the opposite ends of the length of suture. The packaging system includes a tubular element sized to receive and removably hold the pointed ends of the respective needles within its opposite ends, and an envelope including front and back pockets, a top flap and a belt-like portion which is deflectable outwardly from the exterior of the envelope. The envelope can be manipulated between (1) a totally open position wherein the envelope is a flat sheet, (2) a partially closed position wherein the suture anchor is engaged by the belt-like element against the exterior of the envelope, the suture is located in a coil within the front pocket and the needles joined by the tubular element are located in the back pocket, and (3) a totally closed position wherein the top flap is folded over the open ends of the pockets.

9 Claims, 5 Drawing Sheets

SUTURE ANCHOR ASSEMBLY PACKAGING SYSTEM

FIELD OF THE INVENTION

The present invention relates generally to packaging systems. More particularly, the present invention relates to a system and method for packaging a pre-assembled suture anchor assembly of the sort comprising a suture anchor adapted to anchor a portion of a suture in bone, a length of suture and a pair of surgical needles.

BACKGROUND OF THE INVENTION

Pre-assembled suture anchor assemblies of the sort comprising a suture anchor adapted to anchor a portion of a suture in bone, a length of suture and at least one surgical needle are known in the art. In such assemblies, one end of the anchor is typically provided with a bore through which the suture is threaded, and the needles are attached to the opposite ends of the suture. By pre-assembling these components together as a single unit prior to sterilization and packaging, the several components of the suture anchor assembly need not be separately unpackaged and assembled either immediately prior to or during a surgical procedure. In addition, the danger of operating room personnel dropping or misplacing a component, particularly a small suture anchor, is minimized.

Packaging systems for such pre-assembled suture anchor assemblies are also known in the art. For example, one such system is disclosed in U.S. Pat. No. 5,078,730, entitled "Holder for Suture Anchor Assembly", the specification and drawings of which are hereby incorporated herein by reference. In that system, a holder (typically formed out of a plastic block having appropriate surface recesses formed therein) is provided which is adapted to separately and releasably carry the pre-assembled anchor, suture and needle(s). A cover is also provided for selectively covering the outside of the holder and releasably maintaining the pre-assembled components on the holder prior to dismounting for use in a surgical procedure.

The packaging system disclosed in U.S. Pat. No. 5,078,730 has a number of advantages. For one thing, it facilitates sterilization of the pre-assembled suture anchor assembly prior to assembly. In addition, it provides a means for holding the suture anchor steady while it is united with a suture anchor installation tool. Furthermore, it releases the suture in a controlled fashion after the suture anchor is removed from the holder, thereby minimizing tangling problems. Finally, it continues to shield the needle(s) from both operating room personnel and the patient after the suture anchor and most of the suture have been removed from the holder, releasing the needles from their holder positions only in response to a deliberate action to accomplish the same.

OBJECTS AND SUMMARY OF THE INVENTION

Accordingly, one object of the present invention is to provide an alternative packaging system for a pre-assembled suture anchor assembly of the sort comprising a suture anchor adapted to anchor a portion of a suture in bone, a length of suture, and at least one surgical needle.

Another object of the present invention is to provide an improved packaging system for a pre-assembled suture anchor assembly which is inexpensive and simple to make, yet facilitates pre-sterilization of the pre-assembled suture anchor assembly, assists in the attachment of the suture anchor to an appropriate installation tool, minimizes suture tangling, and shields both operating room personnel and the patient from sharp needle points until the needles are required at the surgical site.

Still another object of the present invention is to provide a compact and easily stored packaging system which is easily handled by operating room personnel both before and during a surgical procedure.

Yet another object of the present invention is to provide a packaging system for pre-assembled suture anchor assemblies which can be easily disposed of in an environmentally acceptable manner.

And another object of the present invention is to provide a packaging system for pre-assembled suture anchor assemblies which can be used with a wide range of different suture anchor assemblies.

Yet another object of the present invention is to provide a method for packaging pre-assembled suture anchor assemblies efficiently and inexpensively.

These and other objects of the present invention are achieved by the provision of a novel packaging system for pre-assembled suture anchor assemblies of the sort comprising a suture anchor, a length of suture and a pair of surgical needles, where the needles are respectively attached to the opposite ends of the length of suture, and the anchor is threadingly engaged with the suture between its two ends. The novel packaging system generally comprises an envelope for holding the pre-assembled suture anchor assembly, and a tubular element for releasably retaining at least the two pointed ends of the needles prior to use.

More specifically, the envelope comprises first and second substantially rectangular side panels, and first, second, third, fourth and fifth flap panels. Each of the side panels and each of the flap panels has a front surface, a back surface, and upper, lower, left and right side edges. In the preferred embodiment, the first side panel is substantially the same size and shape as the second side panel, and the right side edge of the first side panel is hingedly attached to the left side edge of the second side panel.

The first, second, third and fourth flap panels are also substantially the same size as the first and second side panels. The first flap panel has its right side edge hingedly attached to the left side edge of the first side panel. The second flap panel has its upper side edge hingedly attached to the lower side edge of the first side panel. The third flap panel has its lower side edge hingedly attached to the upper side edge of the second side panel. The fourth flap panel has its left side edge hingedly attached to the right side edge of the second side panel.

The fifth flap panel is size smaller than the aforemention first and second side panels and the first, second, third and fourth flap panels. The upper side edge of the fifth flap panel is hingedly attached to the lower side edge of the second side panel.

The first side panel further includes anchor retention means for holding the suture anchor on the back surface of the first side panel substantially adjacent to the corner formed by the upper and left side edges of the first side panel. Suture retention means are also located on the first side panel adjacent the upper side edge thereof. Furthermore, first flap retention means are located on the first side panel substantially adjacent to the lower side edge thereof. Second flap retention means are located on the second side panel substantially adjacent to the left side edge thereof.

In the preferred embodiment, the envelope is formed out of a single piece of cardboard, flexible plastic or similar material. The anchor retention means in this embodiment comprises a pair of parallel slits formed in the first side panel which permit a belt-like portion of the first side panel to be deflected away from the plane of the first side panel; a suture anchor is slipped between the belt-like portion and the back surface of the first side panel so that the belt-like portion holds the anchor to the back surface of the first side panel. The suture retention means comprises a plurality of narrow slits cut into the upper side edge of the first side panel, with each slit designed to tightly receive a portion of the suture extending away from the suture anchor. The first flap retention means comprises slits formed in the first side panel and adapted to receive and hold the two ends of the upper side edge of the third flap panel. The second flap retention means comprises slits formed in the second side panel and adapted to receive and hold the two ends of the left side edge of the first flap panel.

The envelope is formed by:

(1) locating the front surface of the second flap panel against the front surface of the first side panel, and locating the front surface of the fourth flap panel against the front surface of the second side panel;

(2) locating the front surface of the fifth flap panel against the back surface of the fourth flap panel;

(3) locating the back surface of the second flap panel against the back surface of the fifth flap panel;

(4) locating the front surface of the first flap panel against the back surface of the second side panel, and releasably engaging the first flap panel with the second flap retension means; and (5) locating the front surface of the third flap panel against the back surface of the first side panel, and releasably engaging the third flap panel with the first flap retension means.

Thus it will be seen that the envelope formed by these panels can be manipulated between:

(a) an open position wherein the front surfaces of the first and second side panels face in substantially the same direction;

(b) a partially closed position wherein (i) the front surfaces of the second and fourth flap panels face the front surfaces of the first and second side panels, respectively, (ii) the front surface of the fifth flap panel faces the back surface of the fourth flap panel, (iii) the back surfaces of the second and fifth flap panels face each other, and (iv) the front surface of the first flap panel faces the back surface of the second side panel, and the first flap panel engages the second flap retention means; and (c) a fully closed position wherein, in addition to assuming the configuration of the above-specified partially closed position, the front surface of the third flap panel faces the back surface of the first side panel, and the third flap panel engages the first flap retention means.

The tubular element is formed out of a flexible material such as plastic, and is sized so that at least the pointed ends of the needles may be engagingly inserted into the opposite ends of the tubular element, with the tubular element thereby releasably retaining at least the two pointed ends of the needles prior to use.

The method of packaging a pre-assembled suture anchor assembly in accordance with the present invention includes the following steps:

(1) providing the single piece of panelled material which is used to form the envelope as described above, with the panelled material being laid out flat so that the first and second side panels and the first, second, third, fourth and fifth flap panels all lie in a single plane and have their front surfaces facing in the same direction, and providing the tubular element;

(2) inserting at least the pointed ends of the needles into the opposite ends of the tubular element;

(3) engaging the suture anchor with the anchor retention means and engaging the suture extending from the suture anchor with the suture retention means;

(4) coiling the suture extending between the suture retension means and the needles;

(5) locating the coiled suture on the front surface of the first side panel and locating the needles joined by the tubular element on the front surface of the second side panel; and (6) forming the envelope around the coiled suture and the needles by:

(i) locating the front surfaces of the second and fourth flap panels against the front surfaces of the first and second side panels, respectively, with the suture coil and the needles located respectively therebetween;

(ii) locating the front surface of the fifth flap panel against the back surface of the fourth flap panel;

(iii) locating the back surface of the second flap panel against the back surface of the fifth flap panel;

(iv) locating the front surface of the first flap panel against the back surface of the second side panel, and then releasably engaging the first flap panel with the second flap retention means; and (v) locating the front surface of the third flap panel against the back surface of the first side panel, and then releasably engaging the third flap panel with the first flap retention means.

BRIEF DESCRIPTION OF THE DRAWINGS

These and other objects and features of the present invention will be further disclosed or rendered obvious by the following detailed description of the preferred embodiment of the invention, which is to be considered together with the accompanying drawings wherein.

DETAILED DESCRIPTION OF THE PREFERRED EMBODIMENT

Figure 1:
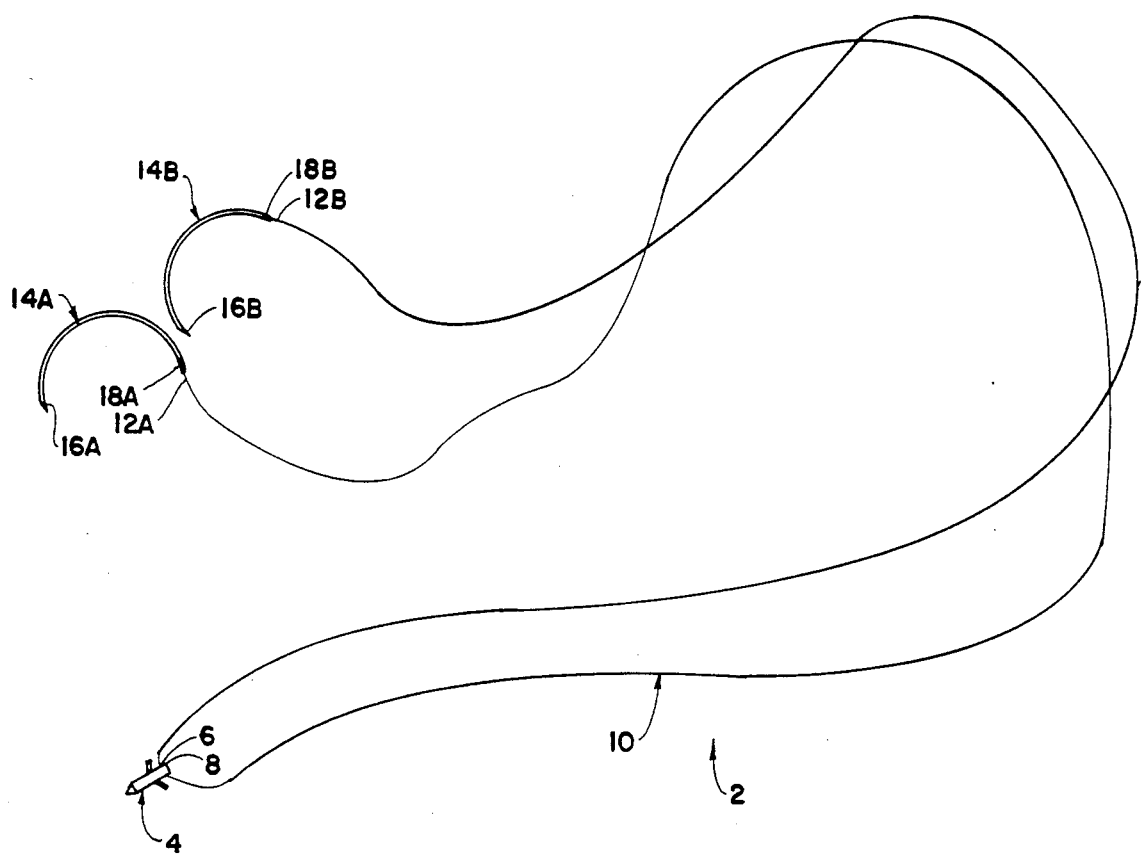
FIG. 1 is a side elevational view of a pre-assembled suture anchor assembly of the sort to be packaged by the present invention.

Referring now to the drawings, and particularly to FIG. 1, there is shown a pre-assembled suture anchor assembly 2 of the sort which is to be packaged by the present invention. Suture anchor assembly 2 comprises a suture anchor 4 having a bore 6 extending through one of its ends 8, a length of suture 10 having a pair of opposite ends 12A, 12B, and a pair of surgical needles 14A and 14B. Needles 14A and 14B are shown in the drawings as being curved surgical needles, however, it will be understood that straight needles could alternatively be provided with suture anchor assembly 2 without departure from the present invention. Each of the needles 14A, 14B includes a pointed end 16A, 16B and a blunt end 18A, 18B. Int he manufacture of suture anchor assembly 2, suture 10 is threaded through bore 6 of anchor 4, and blunt ends 18A, 18B of needles 14A, 14B are attached to the opposite ends 12A, 12B of suture 10, respectively.

Figure 3:
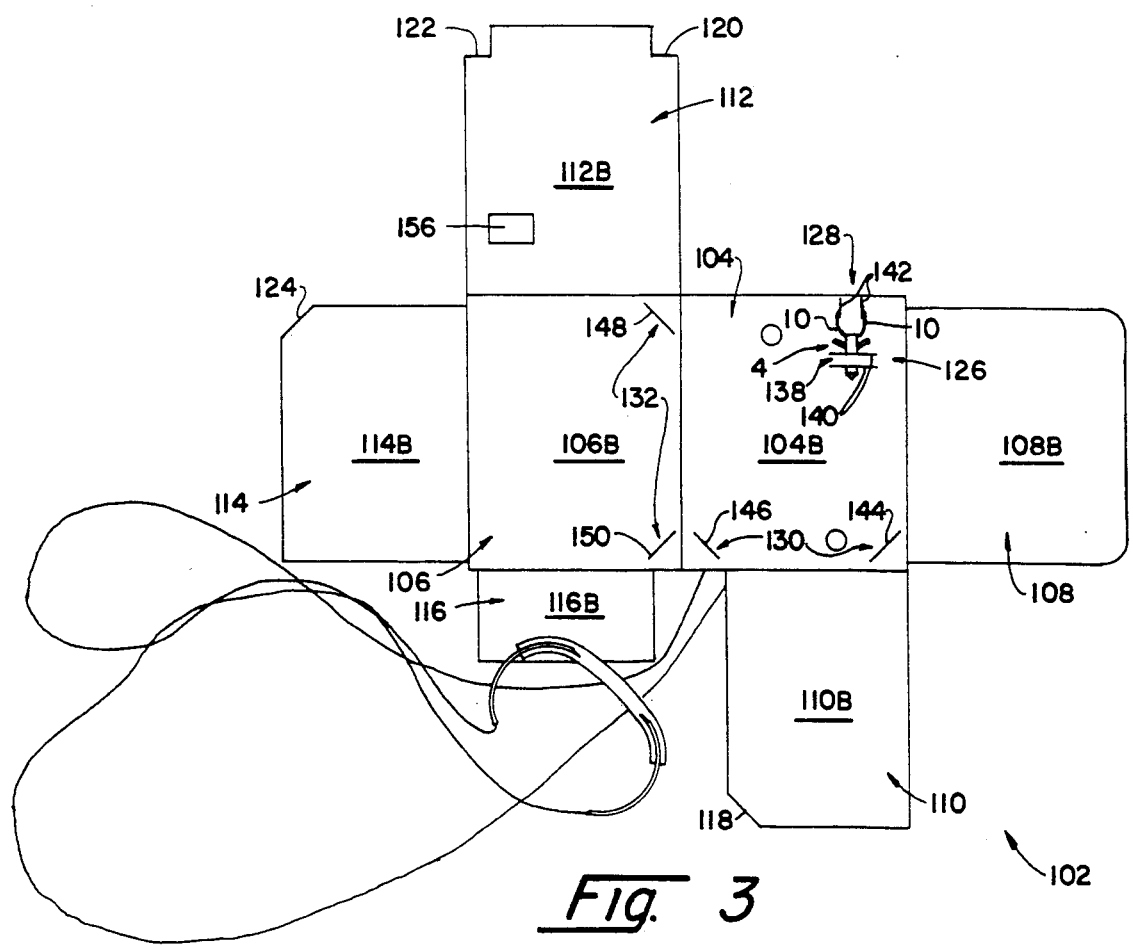
FIG. 3 is a side elevational view showing the back side of the flat piece of panelled material which is used to form the envelope of the present invention.
Figure 4:
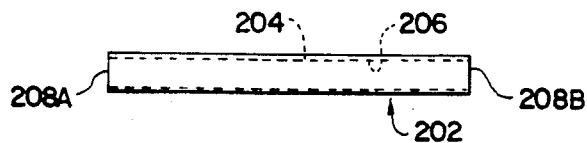
FIG. 4 is a side elevational view of a tubular element provided in accordance with the present invention.
Figure 5:
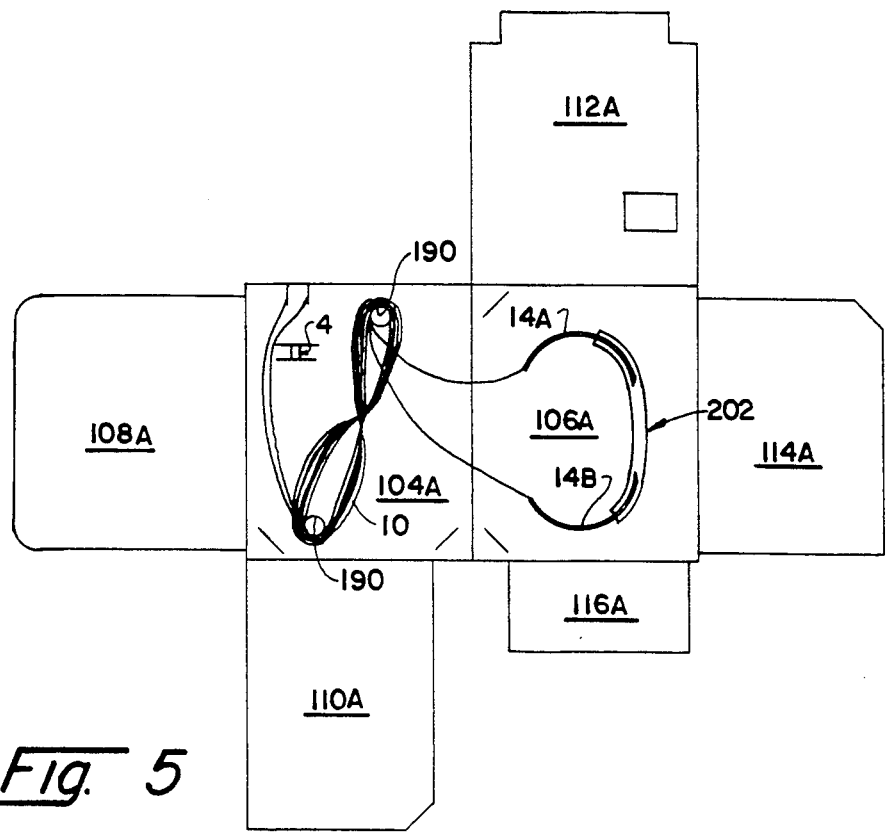
FIGS. 5-9 show the packaging system of the present invention in various degrees of closure.
Figure 6:
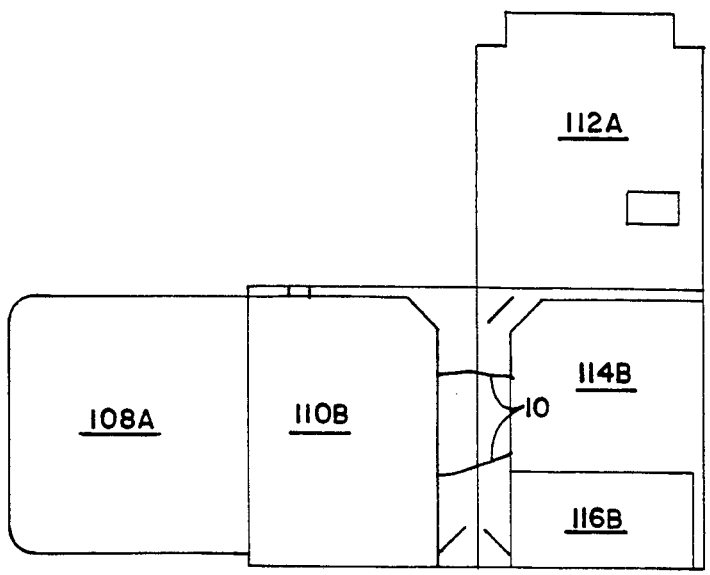
Figure 8:
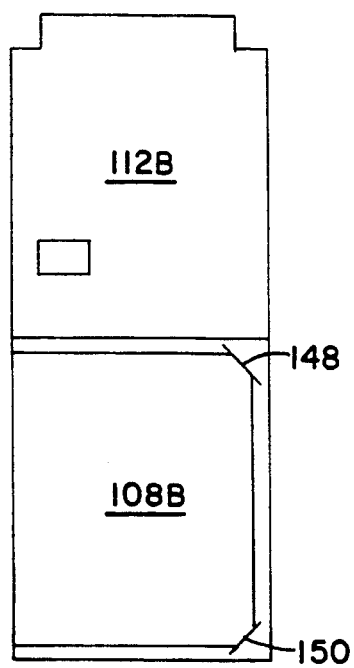
Figure 7:
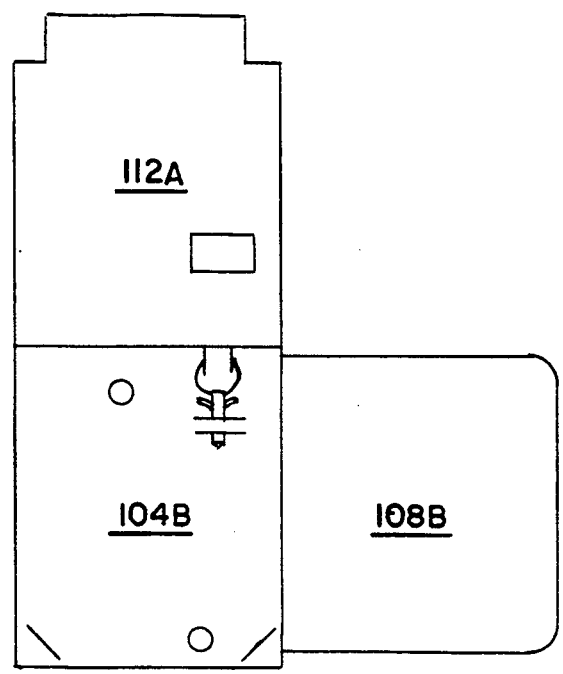
Figure 9:
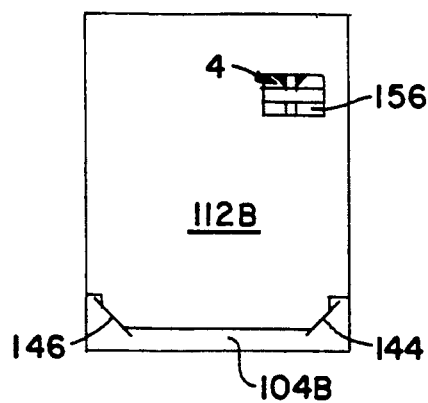

The packaging system of the present invention comprises a novel envelope enclosure 102 (seen in FIGS. 2 and 3 in its unfolded form, in FIGS. 5–8 in various stages of closure, and in FIG. 9 in its final folded form) and a tubular element 202 (best seen in FIG. 4).

Figure 2:
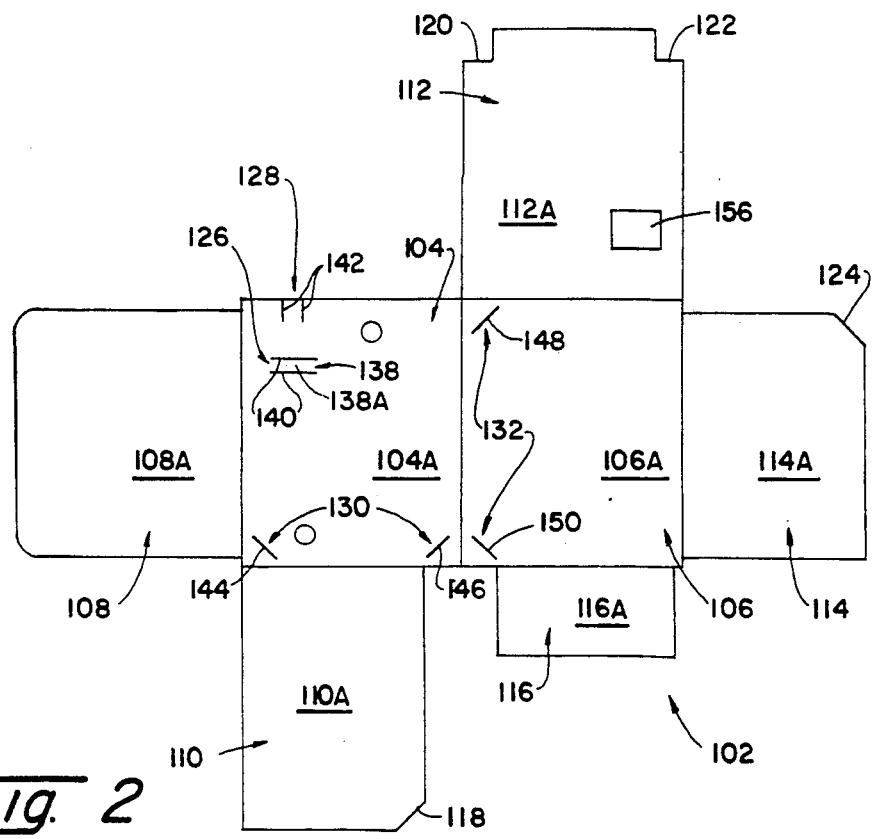
FIG. 2 is a side elevational view showing the front side of the flat piece of panelled material which is used to form the envelope of the present invention.

Looking next at FIGS. 2 and 3, the novel envelope enclosure 102 comprises first and second substantially rectangular side panels 104 and 106, respectively, and first, second, third, fourth and fifth flap panels 108, 110, 112, 114 and 116, respectively. Side panels 104, 106 comprise front surfaces 104A, 106A and rear surfaces 104B, 106B, respectively. Flap panels 108, 110, 112, 114 and 116 comprise front surfaces 108A, 110A, 112A, 114A and 116A and rear surfaces 108B, 11B0, 112B, 114B and 116B, respectively. Each of the side panels 104, 106 and each of the flap panels, 108, 110, 112, 114 and 116 has upper, lower, left and right side edges, as viewed from the front of panels 104, 106, 108, 110, 112, 114 and 116, e.g., as viewed in FIG. 2. For purposes of clarity, this frame of reference for the designations of the upper, lower, left and right side edges of each of the respective panels will be maintained throughout this description. In the preferred embodiment, side panels 104 and 106 are identical in size, and the right side edge of first side panel 104 is hingedly attached to left side edge of second side panel 106.

First, second, third and fourth flap panels 108, 110, 112, and 114 may also be substantially the same size as side panels 104 and 106 or, as shown in FIGS. 2 and 3, they may be made selectively slightly smaller to facilitate folding the various panels, as will hereinafter be discussed in further detail. First flap panel 108 has its right side edge hingedly attached to the left side edge of first side panel 104. Second flap panel 110 has its upper side edge hingedly attached to the lower side end of first side panel 104. Third flap panel 112 has its lower side edge hingedly attached to the upper side edge of second side panel 106. Fourth flap panel 114 has its corresponding left side edge hingedly attached to the right side edge of second side panel 106. Fifth flap panel 116 is preferably formed significantly smaller than first, second, third, and fourth side panels 108, 110, 112 and 114, and the upper side edge of fifth flap panel 116 is hingedly attached to the lower side edge of second side panel 106.

In the embodiment shown, flap panels 108, 110, 112, 114 and 116 are formed smaller than side panels 104 and 106 in order to facilitate folding of the various panels and the formation of a secure envelope. More specifically, first flap panel 108 is formed slightly shorter than side panels 104 and 106, and is centrally hingedly attached to the left side edge of first side panel 104. Second flap panel 110 is narrower than first side panel 104 and is hingedly attached to the lower side edge of first side panel 104 adjacent to the left side edge of side panel 104. Second side panel 110 is also cut away at its lower right corner at 118. Third flap panel 112 is approximately the same size as first and second side panels 104 and 106, except that it is cut away at 120 adjacent the intersection of its left side edge and upper side edge, and cut away at 122 adjacent the intersection of its right side edge and its upper side edge. Fourth flap panel 114 is slightly narrow and slightly shorter than second side panel 106, and is centrally hingedly attached to the right side edge of second side panel 106. Fourth flap panel 114 is also cut away at its upper right corner at 124. Finally, fifth flap panel 116 is smaller in both its height and width dimensions than first and second side panels 104 and 106, and is hingedly attached to the lower side edge of second side panel 106 adjacent to but slightly spaced from the fright side edge of panel 106. As will become more apparent in the following description of the invention, the foregoing sizes and shapes of flap panels 108, 110, 112, 114 and 116 permit the various panels to be folded relative to side panels 104 and 106 and to one another so as to provide a secure packing enclosure for a pre-assembled suture anchor assembly.

Still looking now at FIGS. 2 and 3, first side panel 104 also includes anchor retention means 126 for holding the suture anchor 4 on the back surface 104B of first side panel 104 substantially adjacent to the corner formed by the upper and left side edges of first side panel 104. Suture retention means 128 are located in first side panel 104 adjacent the upper side edge thereof. Furthermore, first flap retention means 130 are located on first side panel 104 adjacent the two lower side corners of first side panel 104. Second flap retention means 132 are located on second side panel 106 adjacent the left side edge of second side panel 106.

In the preferred embodiment, envelope 102 is formed out of a single piece of cardboard, flexible plastic or similar material. In this case, the hinged connections between the various panels may be either scored lines formed in the material along the common boundaries of the panel sections, or so-called living hinges located at those common boundaries. Preferably envelope 102 comprises cardboard of the sort commonly referred to in the industry as suture paper, and the hinged connections between the various panels are scored lines. The anchor retention means 126 in this preferred embodiment comprises a belt-like portion 138 formed in first side panel 104 by a pair of spaced, parallel slits 140. Belt-like portion 138 is adapted to be deflected backwardly, away from back surface 104B of fist side panel 104, so as to capture a suture anchor 4 between surface 138A of portion 138 and the adjoining portions of back surface 104B. Suture retention means 128 of this preferred embodiment comprises a pair of narrow slits 142 cut into the upper side edge of first side panel 104, adjacent the corner formed by the left and top side edges of side panel 104, and adjacent anchor retention means 126. Each of these slits 142 is designed to tightly receive a portion of a suture 10 extending from an anchor 4. First flap retention means 130 preferably comprise a pair of slits 144 and 146 formed in first side panel 104 adjacent its left and right lower corners, respectively, and adapted to receive and old the cutaway corners 122 and 120, respectively, of third flap panels 112, as will hereinafter be described in further detail. Second flap retention means 132 comprise a pair of slits 148 and 150 formed adjacent the upper and lower left side edges of second side panel 106, respectively and adapted to receive the upper and lower left hand corners of first panel flap 108, as will hereinafter be described in further detail.

An aperture 156 extends through third flap panel 112 substantially adjacent to the corner formed by its lower and right side edges. The purpose of aperture 156 is to provide a window for viewing portions of suture anchor 4 and suture 10 of the pre-assembled suture anchor assembly 2 packaged within envelope 102, without opening the packaging itself.

Looking next at FIG. 4, tubular element 202 comprises a length of flexible, preferably transparent plastic tubing having a side wall 204, an internal bore 206, and a first end 208A and a second end 208B. The diameter of bore 206 is slightly smaller than the diameter of the shafts of needles 14A and 14B. Accordingly, pointed end 16A of needle 14A may be inserted into one end 208A of tubular 202, and pointed end 16B of needle 14B may be inserted into the other end 208B of tubular element 202. As this is done, the side wall 204 of tubular element 202 will stretch slightly to accommodate the needle shafts therein. This elastic stretching of the side wall 204 of tubular element 202 effectively grasps the needles 14A and 14B and holds their pointed ends 16A and 16B shielded within the interior of tubular element 202 until a withdrawing force is exerted on the exposed blunt ends 18A and 18B of the needles.

A pre-assembled suture anchor assembly 2 is packaged using envelope 102 and tubular element 202 as follows:

First, the pointed ends 16A and 16B of needles 14A and 14B are inserted into the opposite ends 208A, 208B of tubular element 202, so that the needles are releasably held to tubular element 202 and the pointed ends 16A and 16B of the needles are safely shielded within the interior of tubular element 202.

Next, starting with the envelope 102 in the position shown in FIGS. 2 and 3, i.e., with envelope 102 laid open so that its side panels 104 and 106 and its flap panels 108, 110, 112, 114 and 116 all extend substantially coplaner and have their front surfaces all extending in the same direction, the suture anchor 2 is engaged with anchor engagement means 126 by slipping the body of suture anchor under belt-like portion 138 so that the anchor body is captivated between front side surface 138A and back side surface 104B, and the suture emanating from anchor 4 extends toward suture retention means 128. Then the suture is looped through suture retention mans 128 by passing one length of suture through each of the slits 142, so that the suture lies adjacent front surface 104A of first side panel 104. See generally FIG. 3.

Next, the suture extending between suture retension means 128 and needles 14A, 14B is coiled into a coil 22 on front surface 104A of first side panel 104. Such coiling may conveniently be achieved by positioning a pair of dowels (not shown) through a pair of holes 190 formed in first side panel 104, coiling the suture around the dowels, and then removing the dowels. Alternatively, suture 10 may be coiled into a coil 22 by hand and then laid on front surface 104A of first side panel 104. Needles 14A, 14B, joined by tubular element 202, are then laid on front surface 106A of second side panel 106. See generally FIG. 5.

Then front surface 110A of second flap panel 110 is brought towards front surface 104A of fist side panel 104, so as to capture suture coil 22 therebetween, and fourth flap panel 114 is folded over second side panel 106 so that front surface 114A of fourth flap panel 114 engages front surface 106A of second side panel 106. Then front surface 116A is brought towards back surface 114B of fourth flap panel 114. This action tends to capture needles 14A and 14B to front surface 106A of second side panel 106. See generally FIG. 6.

Next, back surface 110B of second flap panel 110 is placed against back surface 114B of fourth flap panel 114. See generally FIG. 7.

Then front surface 108A of first flap panel 108 is positioned against back surface 106B of second side panel 106, and the two free corners of first flap panel 108 are releasably engaged with second flap retention means 132 by fitting the corners of first flap panel 108 into slits 148 and 150. See generally FIG. 8.

Finally, front surface 112A of third flap panel 112 is positioned against front surface 104B of first side panel 104 and the two free corners of third flap panel 112 are releasably engaged with first flap retension means 130 by fitting corners 120 and 122 into slits 146 and 144, respectively. See generally FIG. 9.

The foregoing procedure provides a suture anchor assembly packaging system which permits portions of anchor 4 and suture 10 to be viewed through window 154 without opening the packaging itself. Envelope 102 and the elements contained therein may then be sterilized prior to being placed inside a further exterior package of the sort well known in the art for shipment.

Thus it will be seen that the envelope formed by these panels can be manipulated between:

(a) an open position wherein front surfaces 104A and 106A of first and second side panels 104 and 106, respectively, face in substantially the same direction (i.e., the position of FIGS. 2 and 3);

(b) a partially closed position wherein (i) front surfaces 110A and 114A of second and fourth flap panels 110 and 114, respectively, face front surfaces 104A and 106A of first and second side panels 104 and 106, respectively, (ii) front surface 116A of fifth flap panel 116 faces back surface 114B of fourth flap panel 114, (iii) back surfaces 110B and 116B of second and fifth flap panels 110 and 116, respectively, face each other, and (iv) front surface 108A of first flap panel 108 faces back surface 106B of second side panel 106 and first flap panel 108 engages second flap retention means 132 (i.e., the position of FIG. 8); and (c) a fully closed position wherein, in addition to assuming the configuration of the above-specified partially closed position, front surface 112A of third flap panel 112 faces back surface 104B of first side panel 104 and third flap panel 112 engages first flap retention means 130.

It will be appreciated that when envelope 102 is in its aforementioned partially closed position, the body of the envelope will essentially comprise a first pocket defined by front surfaces 110A and 104A and holding suture coil 22, and a second pocket defined by front surfaces 114A and 106A and holding needles 14A, 14B, with fifth flap panel 116 closing off the bottom of this pocket. Thus, suture coil 22 and needles 14A, 14B will be isolated from one another by flap panels 110 and 114 when they are held by the envelope. This allows suture 10 to be withdrawn from the envelope without entangling in needles 14A, 14B.

Figure 10:
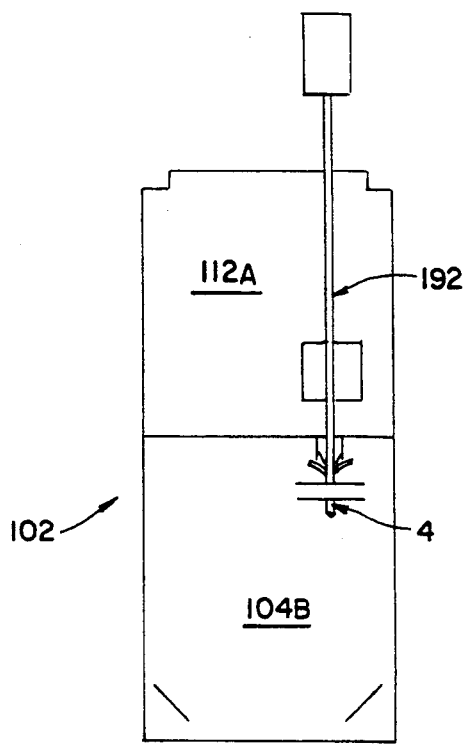
FIGS. 10-12 show the packaging system being opened and the suture anchor assembly being removed from the envelope.
Figure 11:
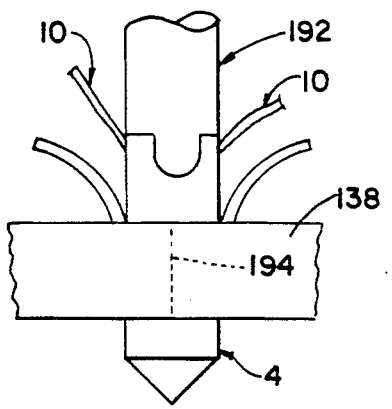
Figure 12:
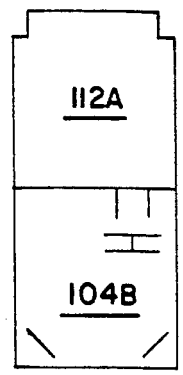
Figure 12:
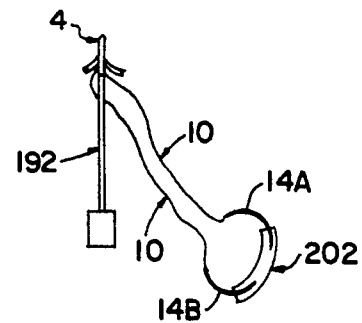

In using the foregoing packaged, pre-assembled suture anchor assembly, the physician simply opens third flap panel 112 to reveal the suture anchor 4 attached to back surface 104B of first side panel 104. From this position, the anchor may either be engaged by an installation tool directly and thereafter removed from anchor retention means 126 while pulling the attached suture 10 out of first suture retention means 128, or the anchor may be removed from its anchor retention means 126 manually, and the suture removed from first suture retention means 128 manually, for subsequent attachment to an installation tool. In the preferred case, anchor 104 is engaged by a tool 192 while the anchor is still held by envelope 102 (FIG. 10) and the anchor is then broken free from envelope 102 by pulling the anchor against a perforation 194 (FIG. 11) formed in belt-like portion 138 so that belt-like portion 138 breaks along its perforation 194 and the anchor is thereby freed from anchor retention means 126 (FIG. 12). In either case, the majority of the suture will remain in envelope 102 along with needles 14A, 14B. Thereafter, as needed, the suture may be pulled out of envelope 102 until the suture and needles 14A, 14B are free from envelope 102. At this point needles 14A, 14B will still be joined by tubular member 202. The needles may then be withdrawn from tubular element 202 for use at the surgical site.

What is claimed is:

1. A packaging system for a suture anchor assembly of the sort comprising a suture anchor, a length of suture and at least one needle, said packaging system comprising:

an envelope comprising first and second substantially rectangular side panels, and first, second, third, fourth and fifth flap panels, each of said side panels and said flap panels having a front surface, a back surface, and upper, lower, left and right side edges;

said first and second side panels being substantially identical to one another in size, and said right side edge of said first side panel being hingedly attached to said left side edge of said second side panel;

said first flap panel having its right side edge hingedly attached to said left side edge of said first side panel, said second flap panel having its upper side edge hingedly attached to said lower side edge of said first side panel, said third flap panel having its lower side edge hingedly attached to said upper side edge of said second side panel, said fourth flap panel having its left side edge hingedly attached to said right side edge of said second side panel, and said fifth flap panel having it supper side edge hingedly attached to said lower side edge of said second side panel;

said first side panel including anchor retention means for holding said suture anchor on said back surface of said first side panel adjacent said upper side edge of said first side panel, suture retention means adjacent said upper side edge thereof, and first flap retention means adjacent said lower side edge thereof;

said second side panel including second flap retention means adjacent said left side edge thereof;

whereby said envelope may be manipulated between:

(a) an open position wherein the front surfaces of said first and second side panels and said first, second, third, fourth and fifth flap panels all face in substantially the same direction and all lie substantially coplanar with one another;

(b) a partially closed position wherein (1) the front surfaces of said second and fourth flap panels face the front surfaces of said first and second side panels, respectively, (2) the front surface of said fifth flap panel faces the back surface of said fourth flap panel, (3) the back surfaces of said second and fifth flap panels face each other, and (4) said front surface of said first flap panel faces said back surface of said second side panel and said first flap panel is engaged by said second flap retention means; and (c) a totally closed position wherein, in addition to assuming the configuration of said partially closed position, said front surface of said third flap panel faces said back surface of said first side panel and said third flap panel is engaged by said first flap retention means.

2. The system of claim 1 wherein said anchor retention means comprises a pair of parallel slits formed in said first side panel, spaced from and extending parallel to said upper side edge thereof, so as to define a belt-like portion adapted to be deflected outwardly from said back surface of said first side panel.

3. The system of claim 1 wherein said suture retention means comprises a pair of parallel slits formed in said first side panel, intersecting and extending perpendicular to said upper side edge thereof.

4. The system of claim 1 wherein said first flap retention means comprises a pair of slits formed in said first side panel, each of said slits being adapted to receive one of the ends of said upper side edge of said third flap panel.

5. The system of claim 1 wherein said second flap retention means comprises a pair of slits formed in said second side panel, each of said slits being adapted to receive one of the ends of said left side edge of said first flap panel.

6. The system of claim 1 wherein said envelope is formed out of suture paper.

7. The system of claim 1 wherein said system is for a suture anchor assembly of the sort comprising at least two needles, said system further comprising:

a tubular element formed out of a flexible material and being sized so that the pointed ends of said needles may be inserted into the opposite ends of said tubular element so as to removably retain at least said pointed ends of said needles within said tubular element.

8. The system of claim 1 wherein said tubular element is formed out of plastic.

9. A method for packaging a suture anchor assembly of the sort comprising suture anchor, a length of suture and a pair of curved needles, said needles being attached at the non-pointed ends thereof to opposite ends of said suture, and said suture threadingly engaging one end of said anchor, said method comprising:

(1) providing a tubular element and an envelope, said tubular element being formed out of a flexible material and sized so that the pointed ends of said needles may be inserted into the opposite ends of said tubular element so as to removably retain at least said pointed ends of said needles within said tubular element;

said envelope comprising first and second substantially rectangular side panels, and first, second, third, fourth and fifth flap panels, each of said side panels and said flap panels having a front surface, a back surface, and upper, lower, left and right side edges;

said first and second side panels being identical to one another in size, and said right side edge of said first side panel being hingedly attached to said left side edge of said second side panel;

said first flap panel having its right side edge hingedly attached to said left side edge of said first side panel, said second flap panel having its upper side edge hingedly attached to said lower side edge of said first side panel, said third flap panel having its lower side edge hingedly attached to said upper side edge of said second side panel, said fourth flap panel having its left side edge hingedly attached to said right side edge of said second side panel, and said fifth flap panel having its upper side edge hingedly attached to said lower side edge of said second side panel;

said first side panel including anchor retention means for holding said suture anchor on said back surface of said first side panel adjacent said upper side edge of said first side panel, suture retention means adjacent said upper side edge thereof, and first flap retention means adjacent said lower side edge thereof;

said second side panel including second flap retention means adjacent said left side edge thereof;

(2) inserting said pointed ends of said needles into said opposite ends of said tubular element;

(3) engaging said suture anchor with said anchor retention means and engaging the suture extending from said suture anchor with said suture retention means;

(4) coiling the suture extending between said suture retention means and said needles;

(5) locating said coiled suture on said front surface of said first side panel and locating said needles joined by said tubular element on said front surface of said second side panel; and (6) forming said envelope around said coiled suture and said needles by:
  (i) locating the front surface of said second and fourth flap panels against the front surface of said first and second side panels, respectively, with the suture coil and said needles located respectively therebetween;
  (ii) locating the front surface of said fifth flap panel against the back surface of said fourth flap panel;
  (iii) locating the back surface of said second flap panel against the back surface of said fifth flap panel;
  (iv) locating the front surface of said first flap panel against the back surface of said second side panel, and then releasably engaging said first flap panel with said second flap retention means; and
  (v) locating the front surface of said third flap panel against the back surface of said first side panel, and then releasably engaging said third flap panel with said first flap retention means.

* * * * *